(12) United States Patent
Sakamoto et al.

(10) Patent No.: US 11,008,330 B2
(45) Date of Patent: May 18, 2021

(54) TETRAPHENYLPORPHYRIN DERIVATIVE

(71) Applicant: KYOTO UNIVERSITY, Kyoto (JP)

(72) Inventors: Masanori Sakamoto, Kyoto (JP); Toshiharu Teranishi, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 16/615,579

(22) PCT Filed: May 22, 2018

(86) PCT No.: PCT/JP2018/019616
§ 371 (c)(1),
(2) Date: Nov. 21, 2019

(87) PCT Pub. No.: WO2018/216679
PCT Pub. Date: Nov. 29, 2018

(65) Prior Publication Data
US 2020/0087315 A1 Mar. 19, 2020

(30) Foreign Application Priority Data
May 22, 2017 (JP) .............................. JP2017-101193

(51) Int. Cl.
C07D 487/22 (2006.01)
H01L 51/00 (2006.01)
H01L 51/42 (2006.01)

(52) U.S. Cl.
CPC ........ C07D 487/22 (2013.01); H01L 51/0077 (2013.01); *H01L 51/426* (2013.01)

(58) Field of Classification Search
None
See application file for complete search history.

(56) References Cited

FOREIGN PATENT DOCUMENTS

| | | |
|---|---|---|
| CN | 105566335 | 5/2016 |
| JP | 2012-506425 | 3/2012 |

(Continued)

OTHER PUBLICATIONS

Yu et al., Indium tin oxide as a semiconductor material in efficient p-type dye-sensitized solar cells. MPG Asia Materials, 2016, 8, e305, 1-7.*

(Continued)

*Primary Examiner* — Po-Chih Chen
(74) *Attorney, Agent, or Firm* — Wenderoth, Lind & Ponack, L.L.P.

(57) ABSTRACT

Provided is a ligand capable of stably bonding together interfaces composed of different types of nanoparticles, different bulk interfaces, or an interface composed of nanoparticles and a bulk interface. A tetraphenylporphyrin derivative represented by the following formula (I):

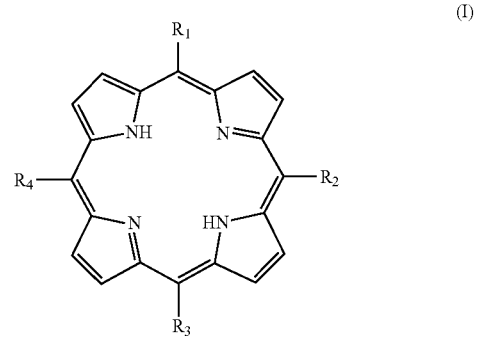

(I)

wherein in formula (I), $R_1$, $R_2$, $R_3$, and $R_4$ are each independently one substituent selected from the group consisting of the following formulas (II) to (VII); and X and Y are any substituents that are different from each other:

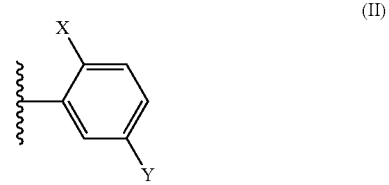

(II)

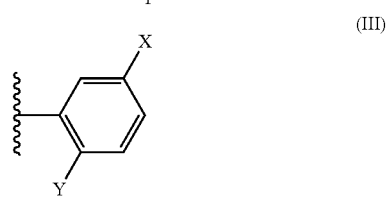

(III)

(IV)

(V)

(VI)

(Continued)

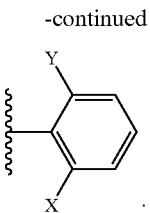

(VII)

5 Claims, 2 Drawing Sheets

(56) References Cited

FOREIGN PATENT DOCUMENTS

| JP | 2012-69560 | 4/2012 |
|---|---|---|
| JP | 2014-236064 | 12/2014 |
| JP | 2015-3866 | 1/2015 |
| WO | 2010/047611 | 4/2010 |
| WO | 2012/029609 | 3/2012 |

OTHER PUBLICATIONS

Chemical Abstract Registry No. 536971-51-4, indexed in the Registry File on STN CAS Online Jun. 25, 2003.*
CAPLUS printout of "Nishino et al., De novo design of artificial membrane proteins on atropisomeric porphyrin" Pept.: Chem., Struct. Biol., Proc. Am. Pept. Symp., 13th (1994), Meeting Date 1993, 1063-1064.*
International Search Report dated Aug. 28, 2018 in International (PCT) Application No. PCT/JP2018/019616.
Takagi et al., "A New Synthetic Model for Myoglobin: "Tulip Garden" Porphyrin", Bulletin of the Chemical Society of Japan, 1985, vol. 58, No. 2, pp. 447-454.
Matile et al., "103. β-Cyclodextrin-Mediated Regioselective Hydrolysis of 5,10,15,20-Tetrakis[2,4-bis(pivaloyloxy)phenyl]-21H,23H-porphine", Helvetica Chimica Acta, 1994, vol. 77, pp. 1087-1098.
Kuroda et al., "Self-induced Porphyrin Dimer Formation via Unusual Atropisomerization of Tetraphenylporphyrin Derivative", Tetrahedron Letters, 1995, vol. 36, No. 46, pp. 8449-8452.
Vilain-Deshayes et al., "Enantiomeric epoxidation of 4-chlorostyrene with $H_2O_2$ catalysed by robust chloromanganese(III)-5,10,15,20-tetrakis-[2-chloro-6-(2,3,4,6-tetraacetyl-O-β-D-glucosyl)phenyl]polphyrins", Journal of Molecular Catalysis A: Chemical, 1996, vol. 113, pp. 201-208.
Rispens et al., "[2.2]-para-Cyclophane-4-carbaldehyde as building-block for chiral ligands, Part II: Epoxidation of alkenes catalyzed by the Mn(III)-complex of an atropoisomerically pure (α, β, α, β,)-tetraarylporphyrin", Journal of Molecular Catalysis A: Chemical, 1998, vol. 136, pp. 13-22.
Monteiro et al., "Synthesis of amphiphilic sulfonamide halogenated porphyrins: MALDI-TOFMS characterization and evaluation or 1-octanol/water partition coefficients", Tetrahedron, 2008, vol. 64, pp. 5132-5138.
Chen et al., "A general approach to L-tyrosine porphyrins", Tetrahedron, 2003, vol. 59, pp. 3505-3510.
Ruzié et al., "Synthesis of 5,10,15,20-tetrakis(2-amino-5-methoxyphenyl)porphyrin: a versatile building block for porphyrin face selection", Tetrahedron Letters, 2004, vol. 45, pp. 1713-1716.
Dunbar et al., "Langmuir-Schaefer films of five different free base tetraphenylporphyrins for optical-based gas sensing of $NO_2$", Sensors and Actuators B, 2008, vol. 128, pp. 468-481.
Numata et al., "Two-dimensional self-assembly of amphiphilic porphyrins on a dynamically shrinking droplet surface", Organic & Biomolecular Chemistry, 2014, vol. 12, pp. 1627-1632.
Lohse et al., "Discrete multiporphyrin pseudorotaxane assemblies from di-•and tetravalent porphyrin building blocks", Beilstein Journal of Organic Chemistry, 2015, vol. 11, pp. 748-762.
Golf et al., "Synthesis of $SF_5$-Substituted Tetrapyrroles, Metalloporphyrins, BODIPYs, and Their Dipyrrane Precursors", The Journal of Organic Chemistry, 2015, vol. 80, pp. 5133-5143.
Sun et al., "Influence of receptor flexibility on intramolecular H-bonding interactions", Organic & Biomolecular Chemistry, 2015, vol. 13, pp. 8053-8066.
Nishino et al., "Aminoporphyrinic Acid as a New Template for Polypeptide Design", Journal of the Chemical Society, Chemical Communications, 1993, pp. 162-163.

* cited by examiner

- Xe lamp MAX303
- Light intensity: 185 mW (422 LP)
- Measured voltage: 0 V vs. Ag$^+$/Ag
- Solution: 1 M KOH aqueous solution

TETRAPHENYLPORPHYRIN DERIVATIVE

TECHNICAL FIELD

The present invention relates to a tetraphenylporphyrin derivative.

BACKGROUND ART

In recent years, research has been actively conducted on the application of nanoparticles, using their properties, to LEDs, photoelectric conversion elements, micro-energy conversion systems, and the like.

Organic ligands protecting nanoparticles are important elements that can control the function, structure, etc., of nanoparticles. If a technology capable of selectively bonding different types of nanointerfaces using ligands is developed, it is considered possible to apply it to various uses, such as single-particle electronics and energy conversion, by functional integration.

Specifically, it is considered that such an organic ligand can be interposed between interfaces of different types of nanoparticles, for example, by applying a solution of the ligand, so that both interfaces are stably bonded together, without being affected by the state of the nanoparticle interface.

However, it was not easy to stably bond interfaces of different types of nanoparticles.

SUMMARY OF INVENTION

Technical Problem

In view of the above circumstances, an object of the present invention is to provide a ligand capable of stably bonding together surfaces comprising different types of nanoparticles, different bulks, or a surface comprising nanoparticles and a bulk.

Solution to Problem

The present inventors conducted extensive research to achieve the above object, and consequently found that a tetraphenylporphyrin derivative solution having a predetermined chemical structure was capable of stably bonding together surfaces comprising different nanoparticles, different bulk interfaces, or a surface comprising nanoparticles and a bulk interface. Upon further research based on this finding, the present inventors have completed the present invention.

Specifically, the present invention provides the following tetraphenylporphyrin derivatives.

Item 1. A tetraphenylporphyrin derivative represented by the following formula (I):

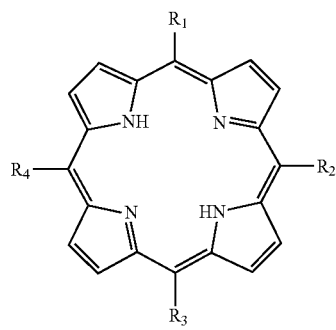

(I)

wherein in formula (I), $R_1$, $R_2$, $R_3$, and $R_4$ are each independently one substituent selected from the group consisting of the following formulas (II) to (VII); and X and Y are any substituents that are different from each other:

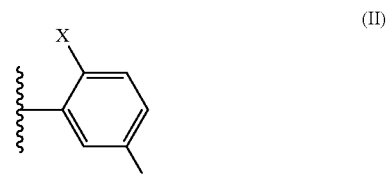

(II)

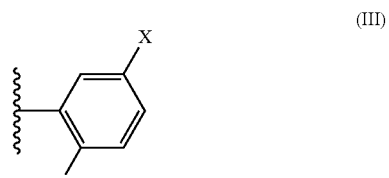

(III)

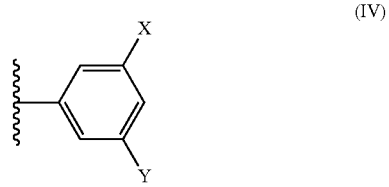

(IV)

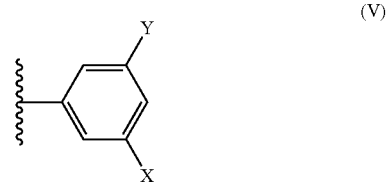

(V)

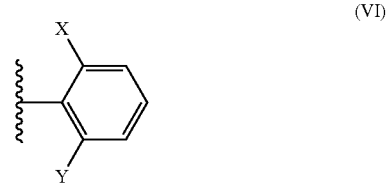

(VI)

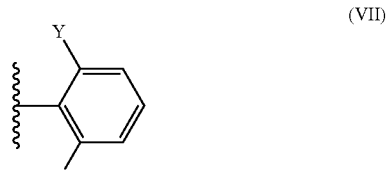

(VII)

Item 2. The tetraphenylporphyrin derivative according to Item 1, wherein in formulas (II) to (VII), X and Y are substituents having the ability to coordinate surfaces;

a first surface for which X has coordination ability and a second surface for which Y has coordination ability are different from each other; and each of the first interface and the second interface is a surface comprising one or more members selected from the group consisting of metal nanoparticles, semiconductor nanoparticles, and organic matter nanoparticles, or a bulk interface comprising one or more members selected from the group consisting of metals, semiconductors, and organic matter.

Item 3. The tetraphenylporphyrin derivative according to Item 1 or 2, wherein in formula (I), $R_1$, $R_2$, $R_3$, and $R_4$ are all the same, and are each any one of formulas (II) to (VII).

Item 4. The tetraphenylporphyrin derivative according to Item 2 or 3, wherein in formulas (II) to (VII), X and Y are each independently one member selected from the group consisting of a thiol group, an amino group, a carboxy group, a catechol group, a vinyl group, an acetylene group, a trimethoxysilyl group, a triethoxysilyl group, a nitro group, and the following formulas (A) to (V):

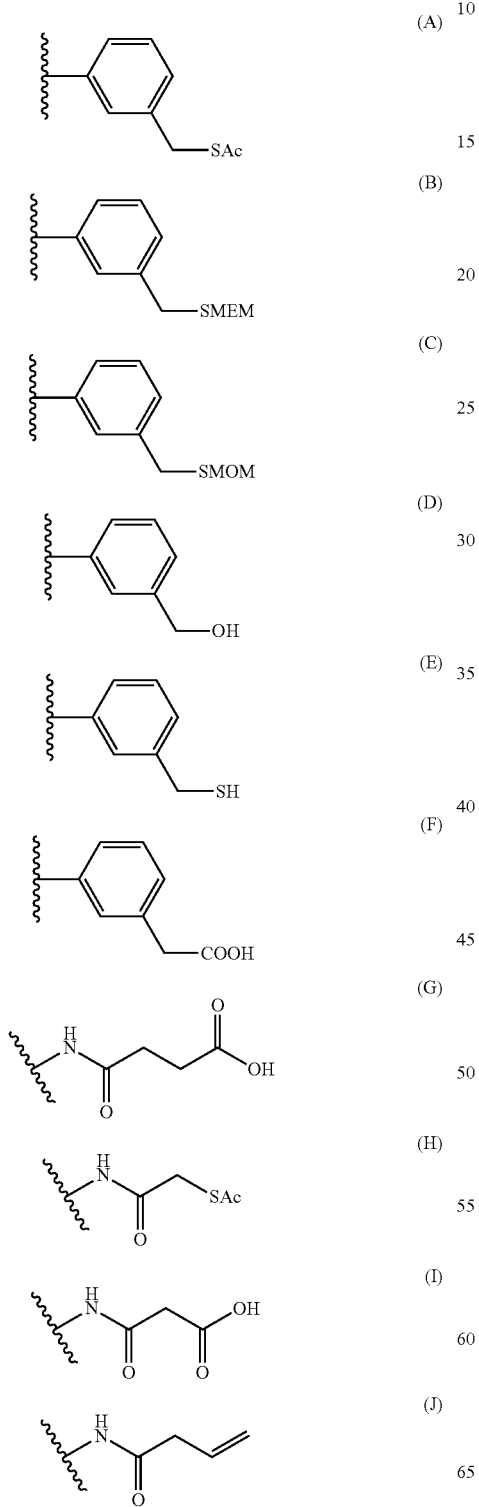
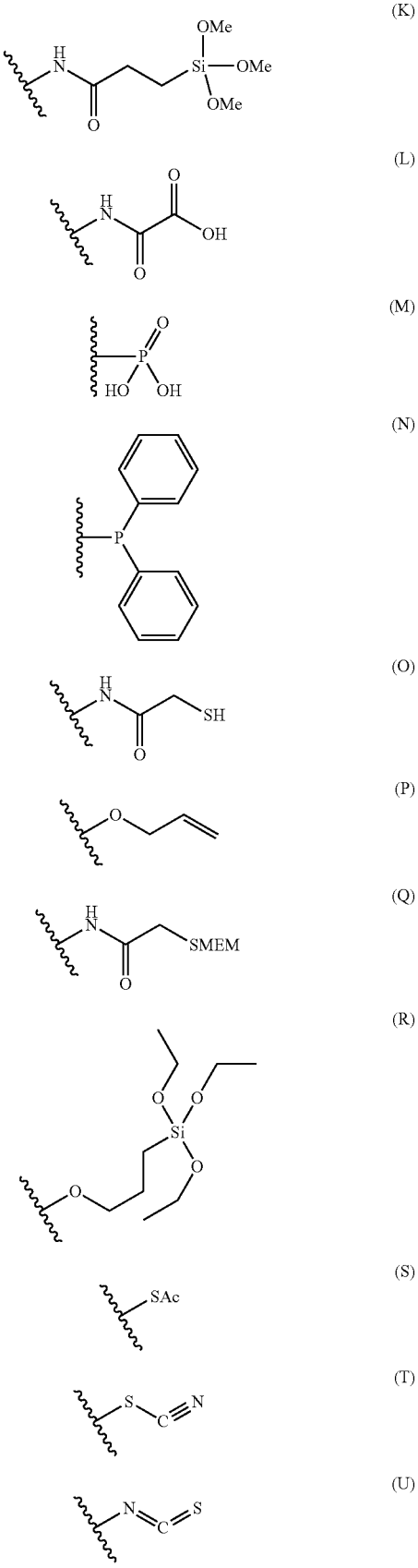

-continued

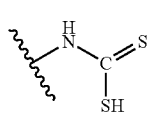
(V)

Item 5. The tetraphenylporphyrin derivative according to Item 2 or 3, wherein in formulas (II) to (VII), X and Y are each any of formulas (E) and (F), formulas (F) and (K), formula (F) and an amino group, an amino group and a catechol group, formula (E) and an amino group, formula (P) and a nitro group, formula (P) and an amino group, formulas (Q) and (R), formula (S) and an amino group, formulas (S) and (U), and formulas (S) and (V).

Item 6. A complex comprising the tetraphenylporphyrin derivative according to any one of Items 1 to 5 and one or more nanoparticles selected from the group consisting of metals, semiconductors, and organic matter.

Item 7. A photoelectric conversion element having the complex according to Item 6.

Advantageous Effects of Invention

According to the tetraporphyrin derivative of the present invention, interfaces composed of different types of nanoparticles can be stably bonded to each other.

DESCRIPTION OF EMBODIMENTS

Figure 1:
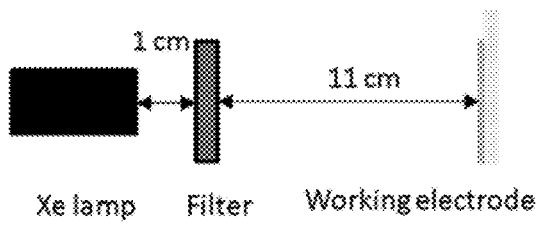
FIG. 1 is an explanatory drawing of a test method of a photoelectric conversion evaluation test.

The present invention is described in detail below.
1. Compound of Formula (I)

The compound of the present invention is represented by the following formula (I):

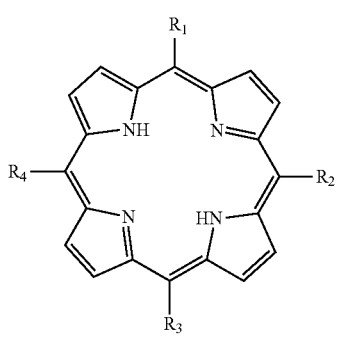
(I)

wherein in formula (I), $R_1$, $R_2$, $R_3$, and $R_4$ are each independently one substituent selected from the group consisting of the following formulas (II) to (VII); and X and Y are any substituents that are different from each other:

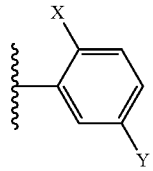
(II)

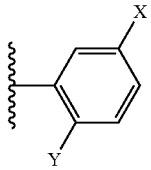
(III)

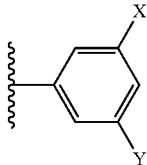
(IV)

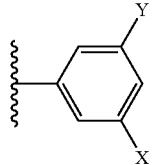
(V)

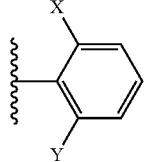
(VI)

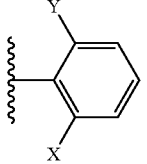
(VII)

The compound represented by formula (I) contributes to the stable bonding between interfaces composed of different types of nanoparticles, and was newly found by the present inventors.

In formulas (II) to (VII), X and Y are substituents having the ability to coordinate surfaces comprising nanoparticles or bulk interfaces. The substituent located at X and the substituent located at Y are preferably different from each other. This structure makes it possible to suitably bond together surfaces for which X and Y respectively have coordination ability.

Further, the nanoparticles in the present specification are preferably one or more members selected from the group consisting of metal nanoparticles, semiconductor nanoparticles, and organic matter nanoparticles.

X and Y are preferably substituents having the ability to coordinate the various types of nanoparticles described above.

Examples of substituents having such properties include a thiol group, an amino group, a carboxy group, a catechol group, a vinyl group, an acetylene group, a trimethoxysilyl group, a triethoxysilyl group, and a nitro group.

Other substituents include substituents represented by the following structural formulas:

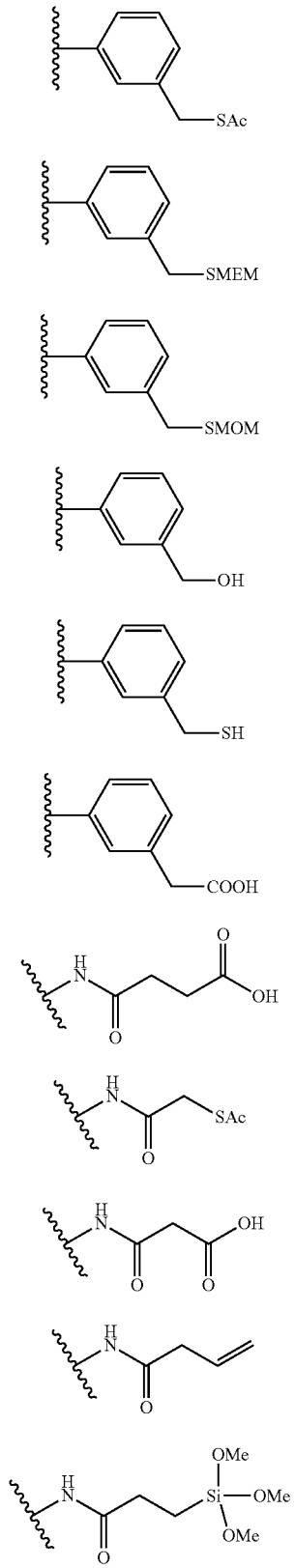
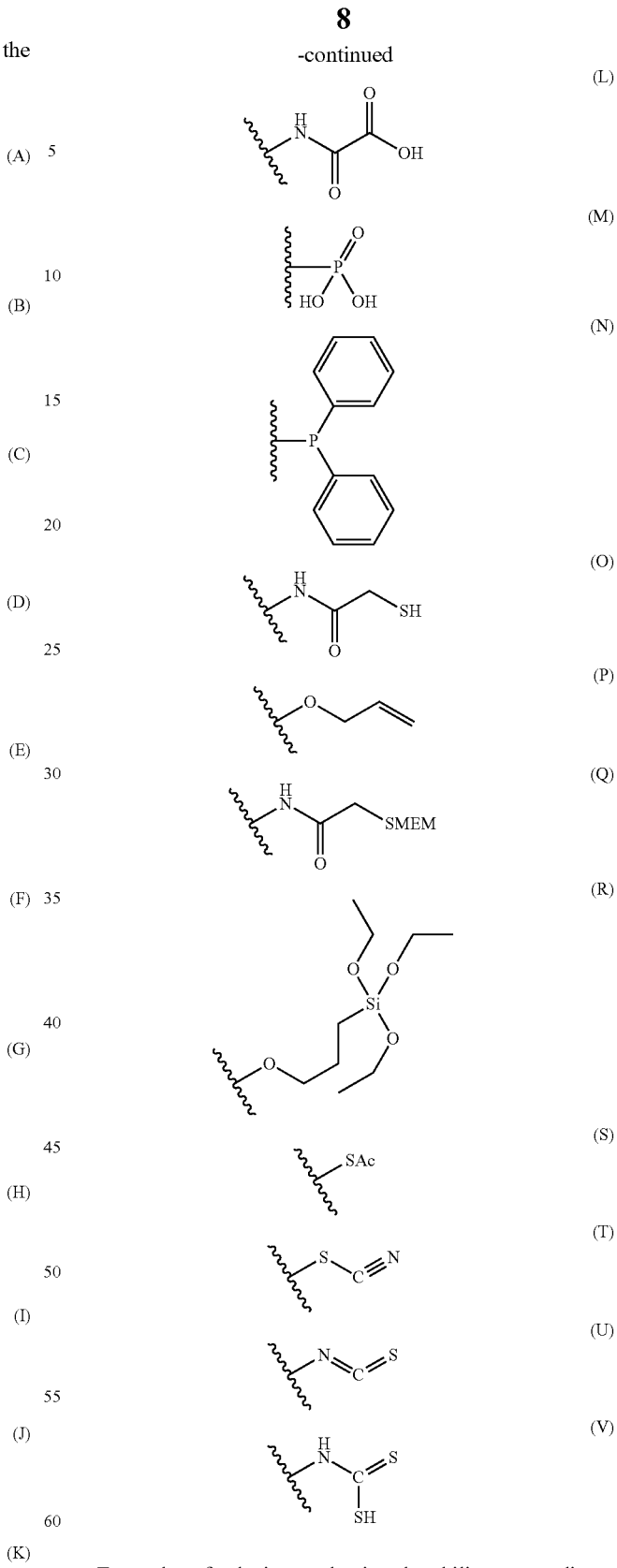

Examples of substituents having the ability to coordinate metal nanoparticles include a thiol group, an amino group, a carboxyl groups, a thioacetyl group, a dithiocarbamate group, an isothiocyanate group, a thiocarbonyl group, and substituents represented by the above formulas (A) to (C), (E) to (I), (L) to (O), (Q), and (S) to (V). As metal nanoparticles, more specifically, well-known metal nanoparticles, such as gold nanoparticles, can be widely used.

Preferable examples of semiconductor nanoparticles include oxide semiconductor nanoparticles, sulfide semiconductor nanoparticles, selenide semiconductors, telluride semiconductors, phosphide semiconductors, and solid solutions thereof. Examples of substituents having the ability to coordinate oxide semiconductor nanoparticles include an amino group, a catechol group, and substituents represented by formulas (D), (F), (G), (I), (K) to (O), and (Q) to (V). As such oxide semiconductor nanoparticles, known oxide semiconductor nanoparticles, such as titanium oxide nanoparticles, can be widely used.

Examples of substituents having the ability to coordinate sulfide semiconductor nanoparticles include an amino group, a carboxyl group, a dithiocarbamate group, an isothiocyanate group, a thiocarbonyl group, and substituents represented by formulas (A) to (C), (E) to (I), (K) to (O), (Q), and (S) to (V). As such sulfide semiconductor nanoparticles, known sulfide semiconductor nanoparticles can be widely used.

Further, as selenide semiconductors, telluride semiconductors, phosphide semiconductors, and solid solutions thereof, those that are known can be widely used.

Examples of substituents having the ability to coordinate organic matter nanoparticles include a substituent represented by formula (J).

In terms of easy synthesis, in formula (I), $R_1$, $R_2$, $R_3$, and $R_4$ are all the same, and are each preferably a substituent represented by any of formulas (II) to (VII).

Preferable examples of the combination of substituents represented by X and Y include formulas (E) and (F), formulas (F) and (K), formula (F) and an amino group, an amino group and a catechol group, formula (E) and an amino group, formula (P) and a nitro group, formula (P) and an amino group, formulas (Q) and (R), formula (S) and an amino group, formulas (S) and (U), and formulas (S) and (V).

The compound represented by formula (I) has the ability to coordinate surfaces comprising different nanoparticles or bulk interfaces, and can be preferably used to stably bond together interfaces composed of different nanoparticles, different bulk interfaces, or an interface composed of nanoparticles and a bulk interface.

In the present specification, the surface comprising nanoparticles refers to an interface comprising the nanoparticles mentioned above. Further, in the present specification, the bulk interface refers to an interface, such as a surface comprising one or more members selected from the group consisting of metals, semiconductors, and organic matter.

The compound represented by formula (I) can be preferably used, because it forms, as the so-called Janus porphyrin, a complex and stably bonds together surfaces respectively comprising two of the different types of nanoparticles mentioned above, different bulk interfaces, or a surface comprising nanoparticles and a bulk interface.

The tetraphenylporphyrin derivative of the present invention can be used to stably bond together a carrier transport layer, such as $TiO_2$, provided on the surface of a substrate, such as a glass plate, and a light absorption layer made of metal nanoparticles. The tetraphenylporphyrin derivative of the present invention is dissolved in a solvent, such as dichloromethane, THF, or DMF, at a concentration of 1 µM to 1 mM, and applied or added dropwise to an electrode layer, followed by drying, after which a layer of metal nanoparticles that forms a photoelectric conversion layer is further provided by an appropriate method, whereby a photoelectric conversion element having excellent bonding stability between the electrode layer and the photoelectric conversion layer can be obtained.

The embodiments of the present invention are described above. Needless to say, however, the present invention is not limited to these examples at all and can be implemented in various forms within a range that does not deviate from the gist of the present invention.

EXAMPLES

The embodiments of the present invention are described in more detail below based on Examples; however, the present invention is not limited thereto.

A tetraphenylporphyrin derivative was synthesized according to the following synthesis route outline. The present Examples show examples in which an amino group or an amide group is added to the phenyl group of the tetraphenylporphyrin derivative; however, other substituents mentioned above may be added. Moreover, compounds (d) to (f) in the following synthesis route are Janus porphyrins or precursors thereof that stably bond together interfaces composed of different types of nanoparticles, and were newly found by the present inventors. Compound (e) can also function as the final target of Janus porphyrin, because the amino group itself contained in the structural formula thereof also has the ability to coordinate nanoparticles.

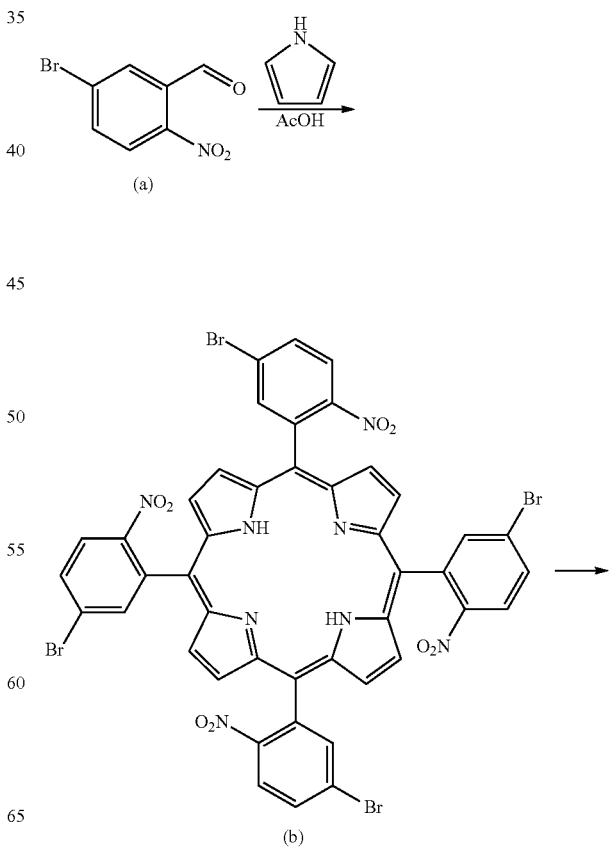

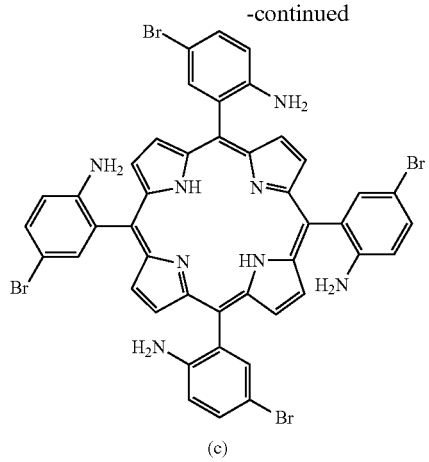

(c)

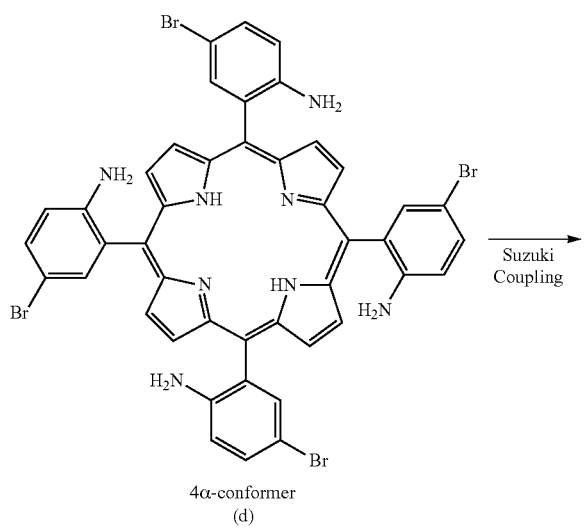

4α-conformer
(d)

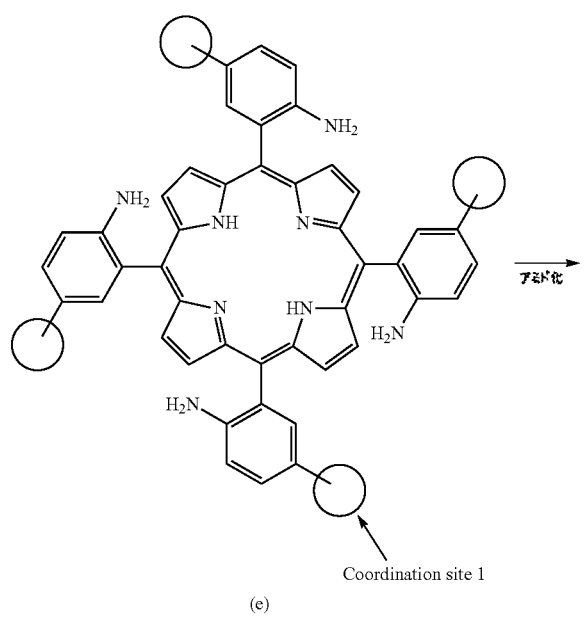

Coordination site 1

(e)

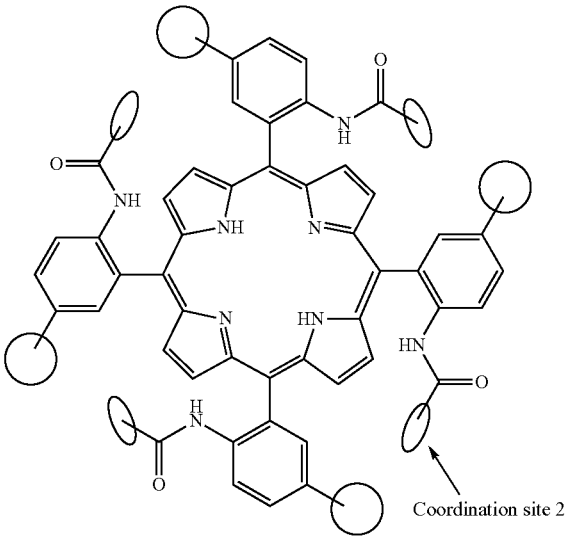

Coordination site 2

(f)

Synthesis of Compound (b)

19.67 g of 5-bromo-2-nitrobenzaldehyde (compound (a) above) was dissolved in acetic acid, and the solution was refluxed. 6 mL of pyrrole was slowly added dropwise to the boiling solution, and boiling was then continued for 30 minutes. At the expiration of 30 minutes from the start of boiling, 33 mL of chloroform was added to the solution in order to avoid the formation of by-products. The solution was naturally returned to room temperature, and then cooled with ice water to 0° C. After standing overnight, the precipitated solid was collected and purified by silica gel chromatography (developing solvent: chloroform) to obtain 3.6 g of compound (b).

(Yield: 15%, MS (MALDI): m/z: 1109 [M]+)

Synthesis of Compound (c)

1 g of compound (b) was dissolved in 100 mL of dichloromethane solution, 10 g of $SnCl_2$ was further added, and the resulting mixture was directly refluxed for 2 hours. 20 mL of 28 mass % aqueous ammonia solution was added to the resulting solution. After stirring, the aqueous phase was discarded, and the dichloromethane phase was removed by an evaporator to obtain 0.4 g of compound (c).

Synthesis of Compound (d)

1 g of compound (c) was dissolved in 10 mL of acetone, and the resulting solution was added to 100 g of silica gel placed in a 500 mL three-necked flask. Further, 200 mL of toluene was added, and the mixture was refluxed for 3 days while flowing nitrogen. After the reaction, the silica gel adsorbed with compound (c) was taken out and flushed with a solution of dichloromethane and acetone (9:1). Thereafter, recrystallization from a chloroform/methanol mixed solution was performed, followed by purification, thereby obtaining a 4α-conformer of compound (d) (yield: 400 mg).

(Yield: 43%, MS (MALDI): m/z: 989 [M]+)

Example 1

200 μmol of compound (d) and 2-(3-(((methoxymethyl)thio)methyl)phenyl)-4,4,5,5-tetramethyl-1,3,2-dioxaborolane (1 mmol) as a phenylboronic acid ether derivative were dissolved in a mixed solvent (25 mL) of 1,2-dimethoxyethane and water (1.5:1). Nitrogen was purged to completely remove oxygen in the solution. Then, while flowing nitrogen, [1,1-bis(diphenylphosphino)-ferrocene]palladium dichloride (20 μmol) and $K_2CO_3$ (1 mmol) were added, and the temperature of the solution was raised to 50° C. and then maintained for 4 hours. Dichloromethane was added to the obtained solution, and washed 3 times with 100 mL of water. The dichloromethane solution was removed by evaporation, and the residue was purified by silica gel column chromatography to obtain a compound of the following formula 1 (yield: 60%, MS (MALDI): m/z: 1340 [M]).

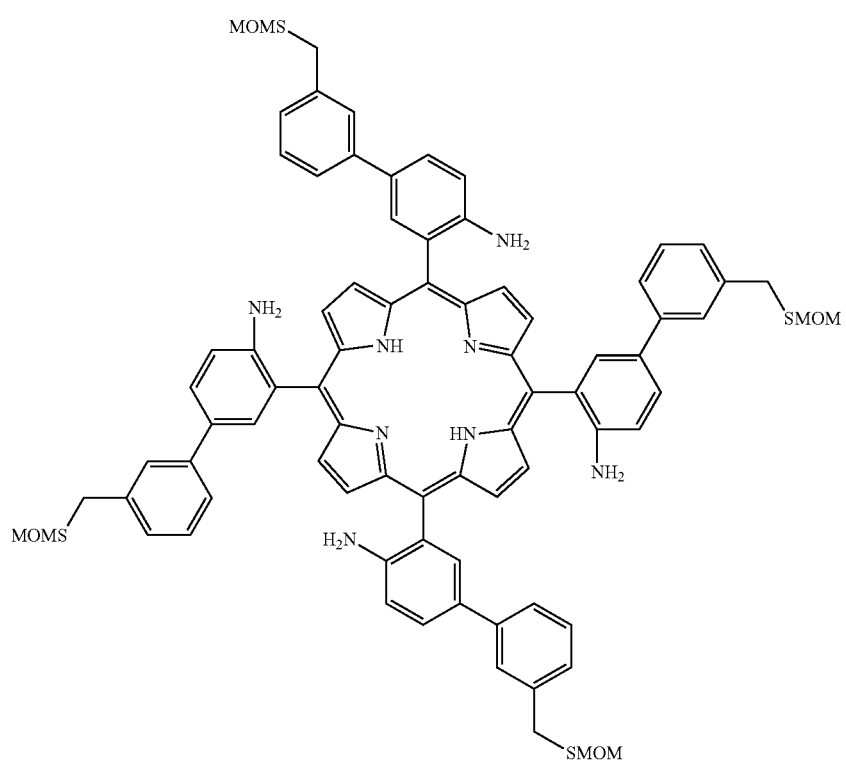

Example 2

The compound represented by the above formula 1 was dissolved in a mixed solvent of dichloromethane and ethanol (2:1), and 10 equivalents of $AgNO_3$ was added. After stirring overnight, the precipitated yellow powder was filtered and washed 3 times with 100 mL of dichloromethane. The powder was then added to 6 N HCl (20 mL), and chloroform (20 mL) was added. After stirring for 4 hours, the chloroform solution was collected and washed with water. Then, the solvent was removed by an evaporator, followed by purification, thereby obtaining a compound of the following formula 2. (Yield: 25%, MS (MALDI): m/z: 1164 [M]+)

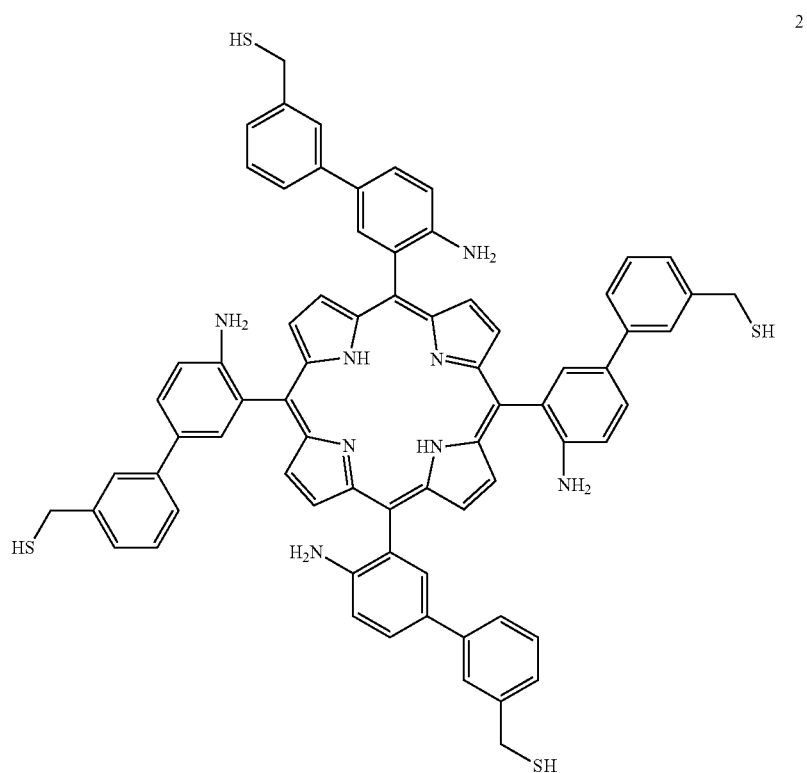 [SMILES: Nc1ccc(-c2cccc(CS)c2)cc1-c1c2nc(c(-c3cc(-c4cccc(CS)c4)ccc3N)c3ccc([nH]3)c(-c3cc(-c4cccc(CS)c4)ccc3N)c3nc(c(-c4cc(-c5cccc(CS)c5)ccc4N)c4ccc1[nH]4)C=C3)C=C2]

2

Example 3
The compound represented by the above formula 2 was dissolved in a dichloromethane solution, and 6 equivalents of acetyl chloride was added, followed by stirring for 2 hours. The solvent was removed by an evaporator, followed by purification, thereby obtaining a compound represented by the following formula 3. (Yield: 96%, MS (MALDI): m/z: 1332 [M]+)
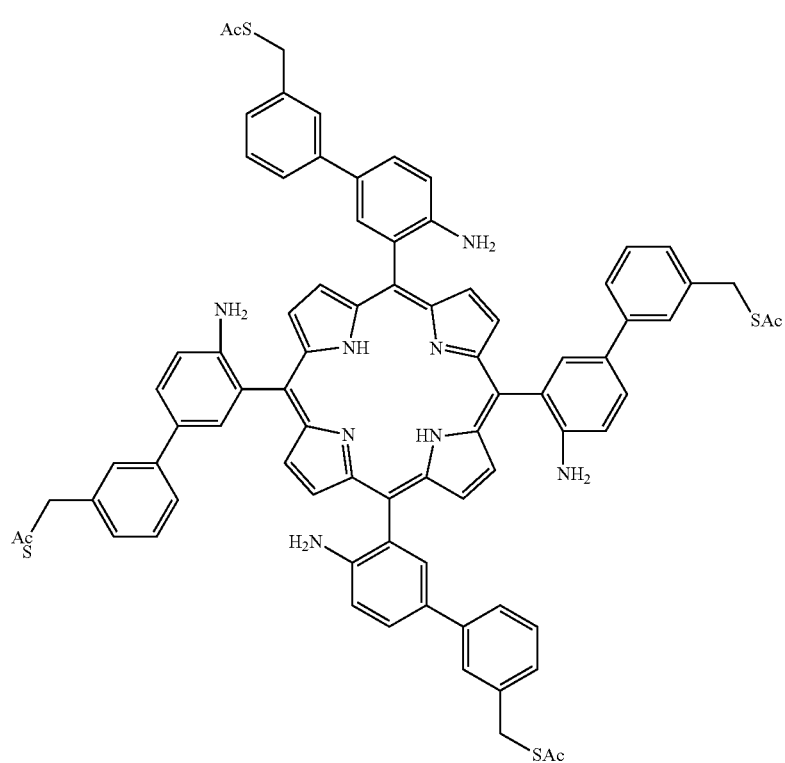
3

Example 4

200 μmol of compound (d) and 2-(4-(tert-butoxy)-3-(((methoxymethyl)thio)methyl)phenyl)-4,4,5,5-tetramethyl-, 3,2-dioxaborolane (1 mmol) as a phenylboronic acid ether derivative were dissolved in a mixed solvent (25 mL) of 1,2-dimethoxyethane and water (1.5:1). Nitrogen was purged to completely remove oxygen in the solution. Then, while flowing nitrogen, [1,1-bis(diphenylphosphino)-ferrocene]palladium dichloride (20 mol) and $K_2CO_3$ (1 mmol) were added, and the temperature of the solution was raised to 50° C. and then maintained for 4 hours. Dichloromethane was added to the obtained solution, and washed 3 times with 100 mL of water. The dichloromethane solution was removed by evaporation, and the residue was purified by silica gel column chromatography to obtain a compound solid. The obtained solid was dissolved in a mixed solvent of dichloromethane and ethanol (2:1), and 10 equivalents of $AgNO_3$ was added. After stirring overnight, the precipitated yellow powder was filtered and washed 3 times with 100 mL of dichloromethane. The powder was then added to 6 N HCl (20 mL), and chloroform (20 mL) was added. After stirring for 4 hours, the chloroform solution was collected and washed with water. Then, the solvent was removed by an evaporator. The obtained solid was dissolved in a dichloromethane solution, and 6 equivalents of acetyl chloride was added, followed by stirring for 2 hours. The solvent was removed by an evaporator, followed by purification, thereby obtaining a compound represented by the following formula 4. (Yield: 10%, MS (MALDI): m/z: 1628 [M]+)

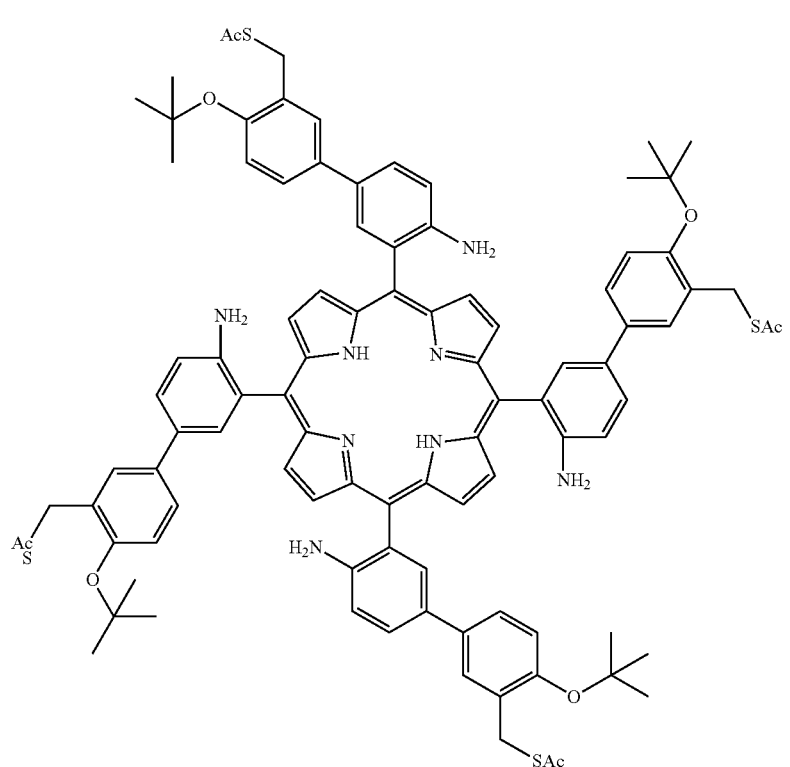

4

Example 5

100 mg of the compound represented by the above formula 1 was dissolved in 20 mL of a mixed solvent of dichloromethane and ethanol (2:1), and 10 equivalents of AgNO₃ was added. After stirring overnight, the precipitated yellow powder was filtered and washed 3 times with 100 mL of dichloromethane. The powder was then added to 6 N HCl (20 mL), and chloroform (20 mL) was added. After stirring for 4 hours, the chloroform solution was collected and washed with water. Then, the solvent was removed by an evaporator to obtain a compound represented by the following formula 5. (Yield: 17%, MS (MALDI): m/z: 1507 [M]+)

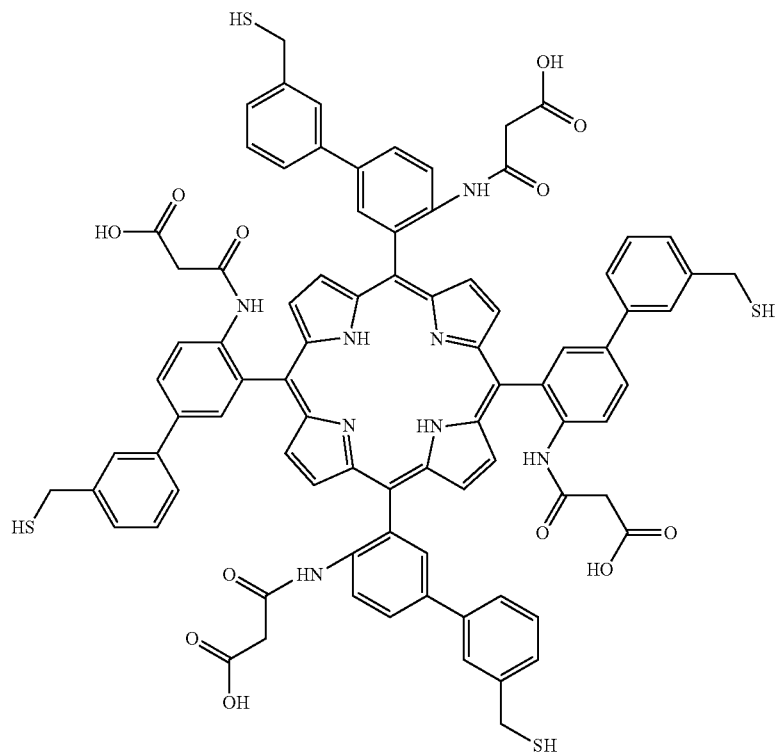

Example 6

200 µmol of compound (d) and 3-(methoxycarbonyl) phenylboronic acid (1 mmol) as a phenylboronic acid derivative were dissolved in a mixed solvent (25 mL) of 1,2-dimethoxyethane and water (1.5:1). Nitrogen was purged to completely remove oxygen in the solution. Then, while flowing nitrogen, [1,1-bis(diphenylphosphino)-ferrocene]palladium dichloride (20 µmol) and $K_2CO_3$ (1 mmol) were added, and the temperature of the solution was raised to 50° C. and then maintained for 4 hours. Dichloromethane was added to the obtained solution, and washed 3 times with 100 mL of water. The dichloromethane solution was removed by evaporation, and the residue was purified by silica gel column chromatography to obtain a compound solid. The obtained solid was dissolved in a mixed solvent of dichloromethane and ethanol (2:1), and the solvent was removed by an evaporator, followed by purification, thereby obtaining a compound represented by the following formula 6. (Yield: 56%, MS (MALDI): m/z: 1211 [M]+)

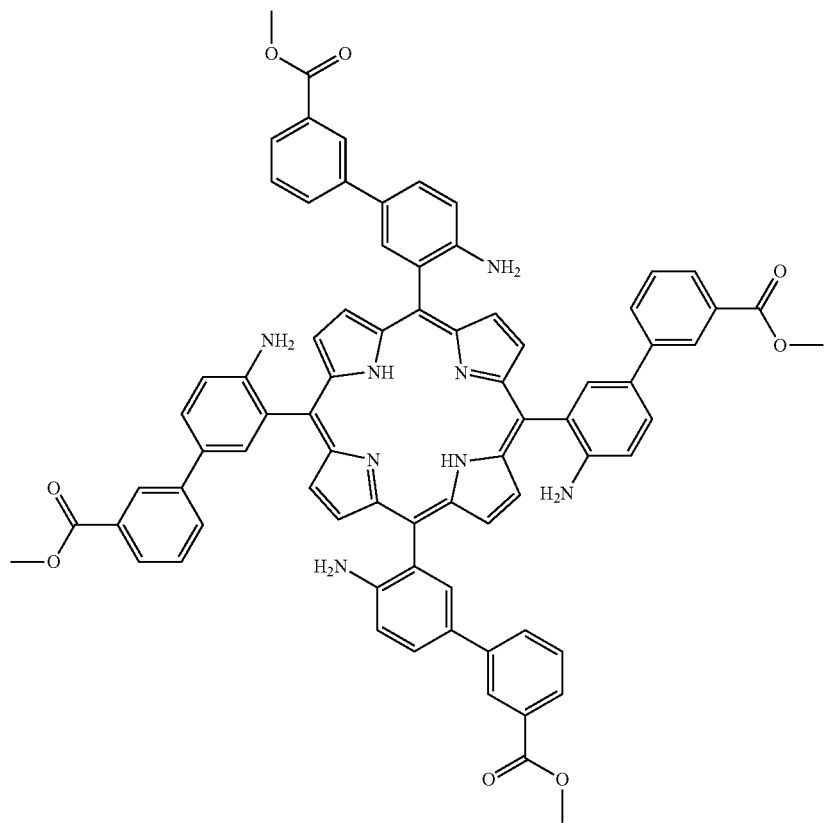

6

Example 7

100 mg of the compound represented by the above formula 6 was dissolved in 5 mL of a mixed solution of a THF solution and KOH (1 N) (5:1), and stirred for 4 hours. The aqueous phase was taken, the pH was adjusted to neutral, and the precipitated solid was collected in dichloromethane. The solvent was removed by an evaporator to obtain a compound represented by the following formula 7. (Yield: 67%, MS (MALDI): m/z: 1332 [M]+)

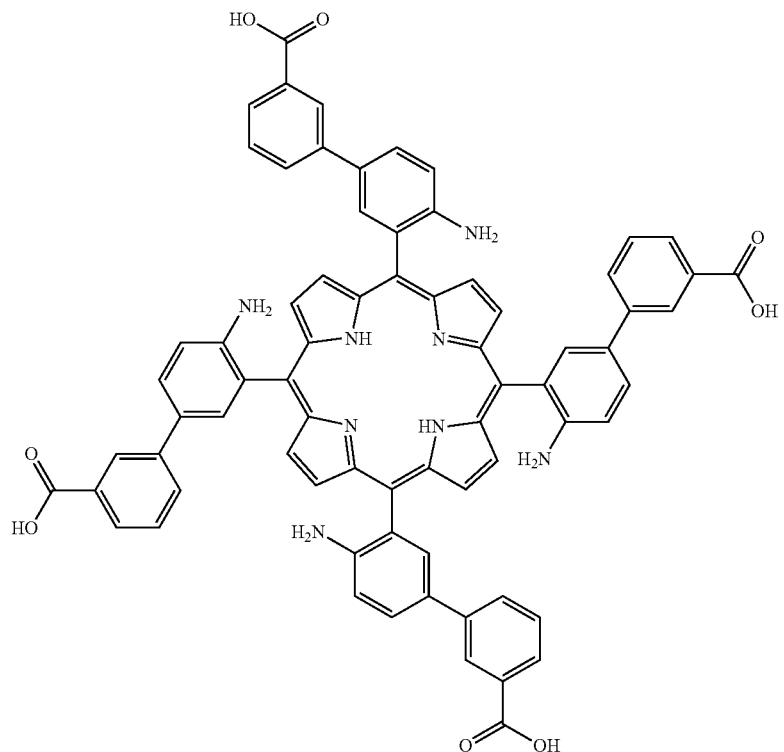

7

Example 8
200 µmol of the compound represented by the above formula 7 was reacted with 1 mmol of acryloyl chloride as an acetyl chloride derivative. The solution used was DMF. Water was added to adjust the pH to weak acidity, and the precipitated solid was collected by filtration to obtain a compound represented by the following formula 8. (Yield: 80%, MS (MALDI): m/z: 1740 [M]+)
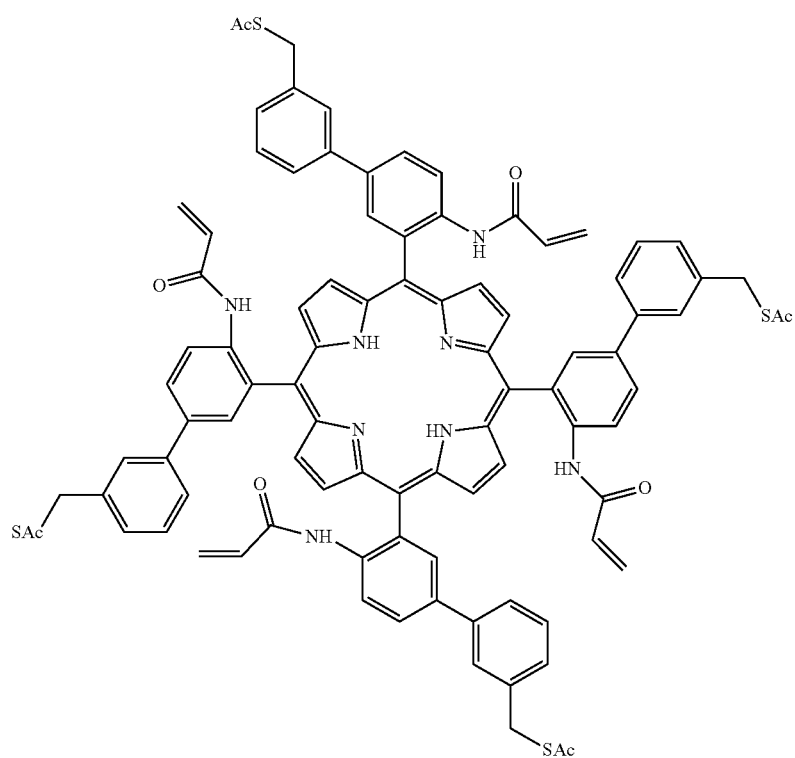
8

Example 9

200 µmol of the compound represented by the above formula 1 was reacted with 1 mmol of methyl malonyl chloride as an acetyl chloride derivative. The obtained product was dissolved in 10 mL of a mixed solution of a THF solution and KOH (1 N) (5:1) and stirred for 4 hours. The aqueous phase was taken, the pH was adjusted to neutral, and the precipitated solid was collected in dichloromethane. The solvent was removed by an evaporator to obtain a compound represented by the following formula 9. (Yield: 40%, MS (MALDI): m/z: 1684 [M]+)

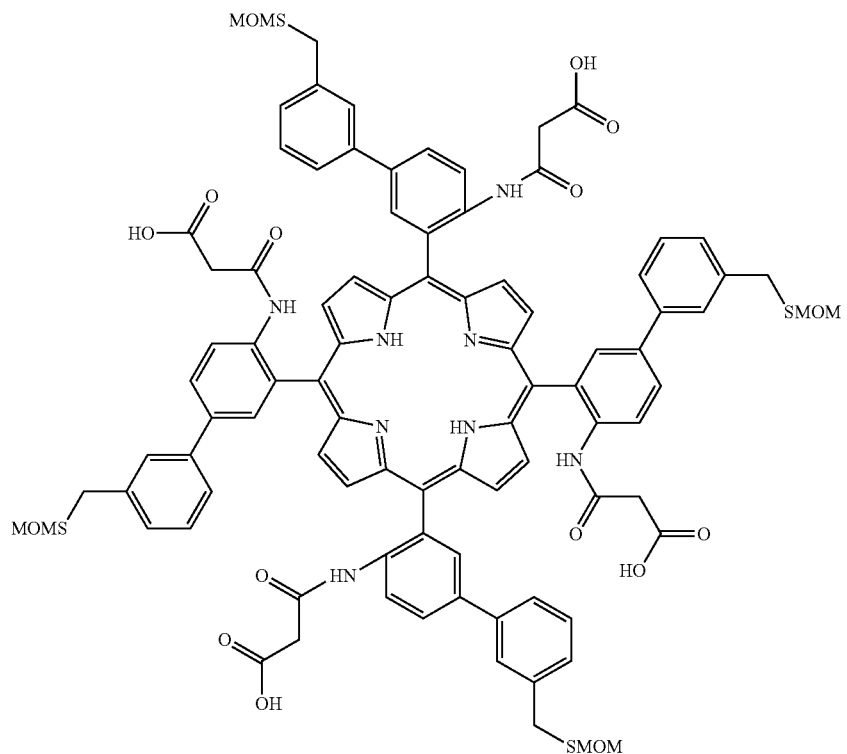

Example 10

200 μmol of the compound represented by the above formula 1 was reacted with 1 mmol of ethyl succinyl chloride as an acetyl chloride derivative. The obtained product was dissolved in 10 mL of a mixed solution of a THF solution and KOH (1 N) (5:1) and stirred for 4 hours. The aqueous phase was taken, the pH was adjusted to neutral, and the precipitated solid was collected in dichloromethane. The solvent was removed by an evaporator to obtain a compound represented by the following formula 10. (Yield: 56%, MS (MALDI): m/z: 1740 [M]+)

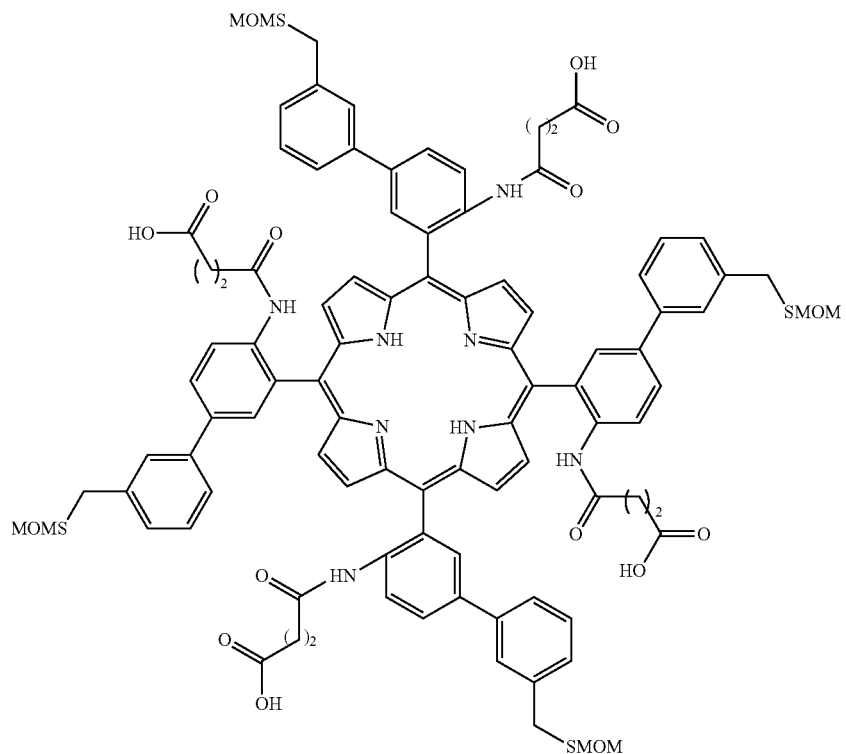

Example 11

100 mg of the compound represented by the above formula 10 was dissolved in 10 mL of a mixed solvent of dichloromethane and ethanol (2:1), and 10 equivalents of AgNO$_3$ was added. After stirring overnight, the precipitated yellow powder was filtered and washed 3 times with 100 mL of dichloromethane. The powder was then added to 6 N HCl (20 mL), and chloroform (20 mL) was added. After stirring for 4 hours, the chloroform solution was collected and washed with water. Then, the solvent was removed by an evaporator to obtain a compound represented by the following formula 11. (Yield: 22%, MS (MALDI): m/z: 1575 [M]+)

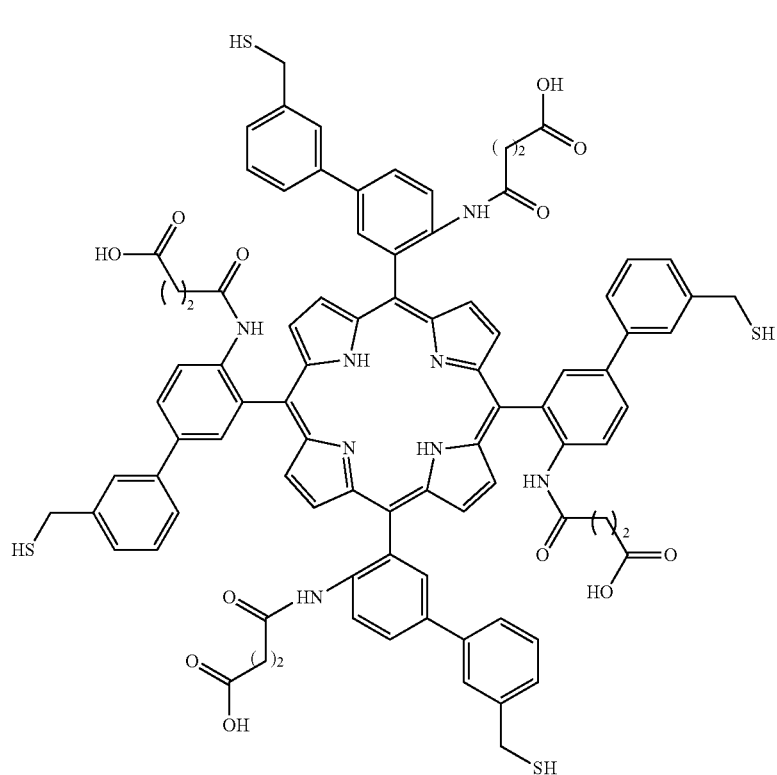

11

Example 12

200 µmol of the compound represented by the above formula 7 was reacted with 1 mmol of S-(2-chloro-2-oxoethyl)ethanethioate as an acetyl chloride derivative. The solution used was DMF. Water was added to adjust the pH to weak acidity, and the precipitated solid was collected by filtration to obtain a compound represented by the following formula 12. (Yield: 66%, MS (MALDI): m/z: 1620 [M]+)

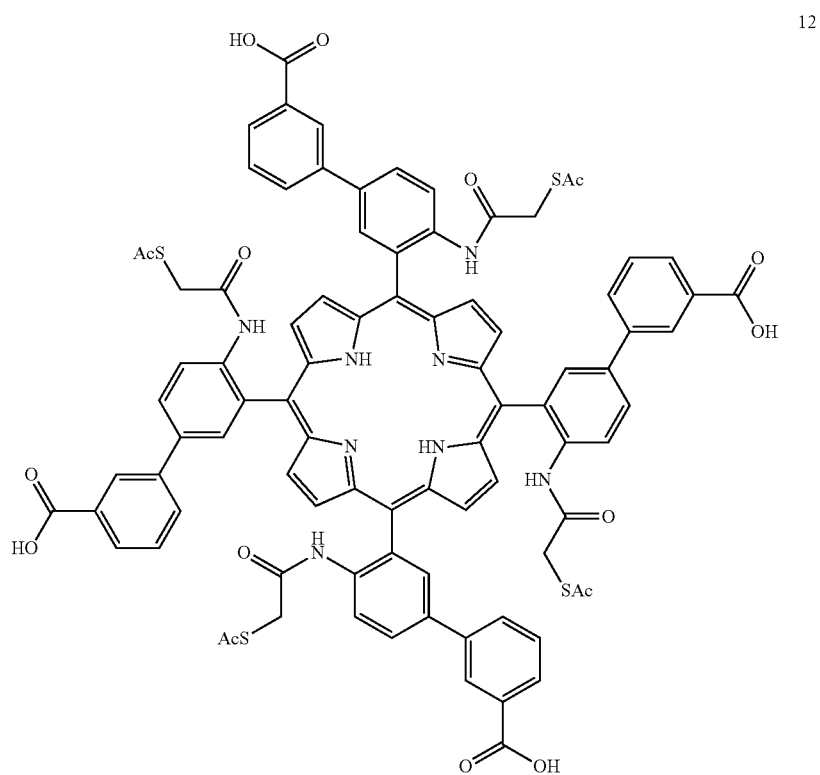

12

Example 13

100 mg of the compound represented by the above formula 3 was dissolved in 10 mL of a dehydration solution of ethanol/diethyl ether (1:1). 10 equivalents of triethoxysilane and a catalytic amount of H₂PtCl₂ were added and reacted. Excess triethoxysilane was removed by an evaporator to obtain a compound represented by the following formula 13. (MS (MALDI): m/z: 2036 [M]+)

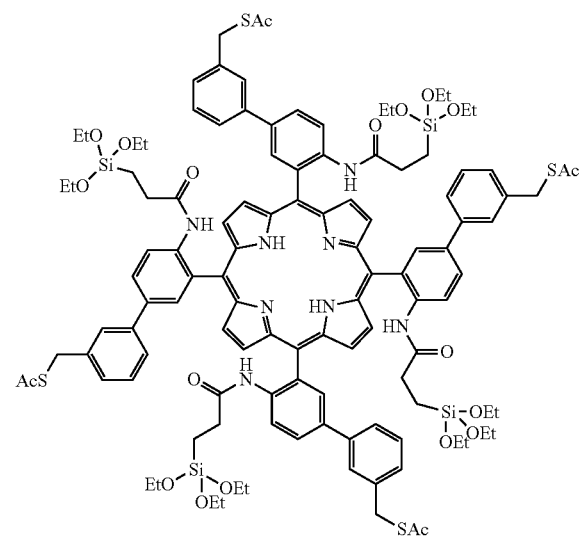

13

Example 14

200 μmol of compound (d) and 2-(3-(((2-methoxyethoxy)methyl)thio)methyl)phenyl)-4,4,5,5-tetramethyl-1,3,2-dioxaborolane (1 mmol) as a phenylboronic acid ether derivative were dissolved in a mixed solvent (25 mL) of 1,2-dimethoxyethane and water (1.5:1). Nitrogen was purged to completely remove oxygen in the solution. Then, while flowing nitrogen, [1,1-bis(diphenylphosphino)-ferrocene]palladium dichloride (20 μmol) and K₂CO₃ (1 mmol) were added, and the temperature of the solution was raised to 50° C. and then maintained for 4 hours. Dichloromethane was added to the obtained solution, and washed 3 times with 100 mL of water. The dichloromethane solution was removed by evaporation, and the residue was purified by silica gel column chromatography to obtain a compound of the following formula 14 (yield: 66%, MS (MALDI): m/z: 1516 [M]).

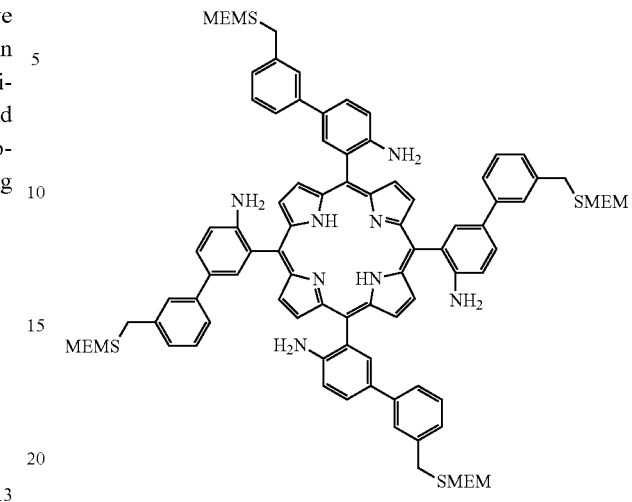

14

Example 15

200 μmol of compound (d) and (3-(4,4,5,5-tetramethyl-1,3,2-dioxaborolan-2-yl)phenyl)methanol (1 mmol) as a phenylboronic acid derivative were dissolved in a mixed solvent (25 mL) of 1,2-dimethoxyethane and water (1.5:1). Nitrogen was purged to completely remove oxygen in the solution. Then, while flowing nitrogen, [1,1-bis(diphenylphosphino)-ferrocene]palladium dichloride (20 μmol) and K₂CO₃ (1 mmol) were added, and the temperature of the solution was raised to 50° C. and then maintained for 4 hours. Dichloromethane was added to the obtained solution, and washed 3 times with 100 mL of water. The dichloromethane solution was removed by evaporation, and the residue was purified by silica gel column chromatography to obtain a compound of the following formula 15 (yield: 10%, MS (MALDI): m/z: 1099 [M]).

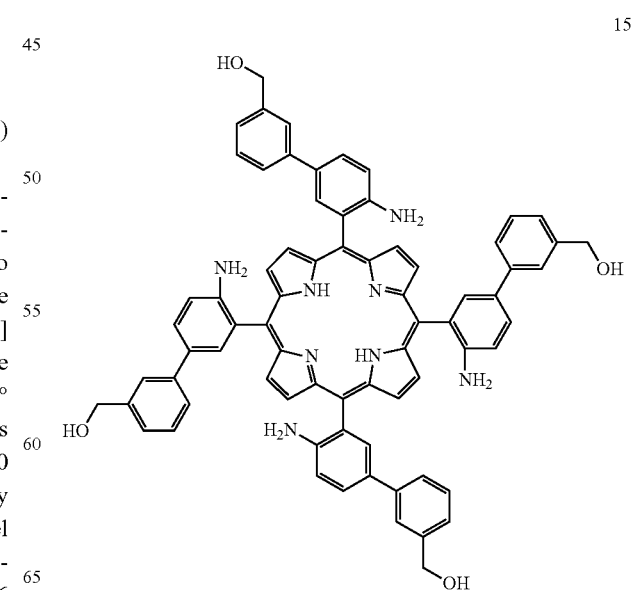

15

Example 16

200 μmol of the compound represented by the above formula 1 was reacted with 1 mmol of methyl chloroglyoxylate as an acetyl chloride derivative. The obtained product was dissolved in 10 mL of a mixed solution of a THF solution and KOH (1 N) (5:1) and stirred for 4 hours. The aqueous phase was taken, the pH was adjusted to neutral, and the precipitated solid was collected in dichloromethane. The solvent was removed by an evaporator to obtain a compound represented by the following formula 16. (Yield: 30%, MS (MALDI): m/z: 1684 [M]+)

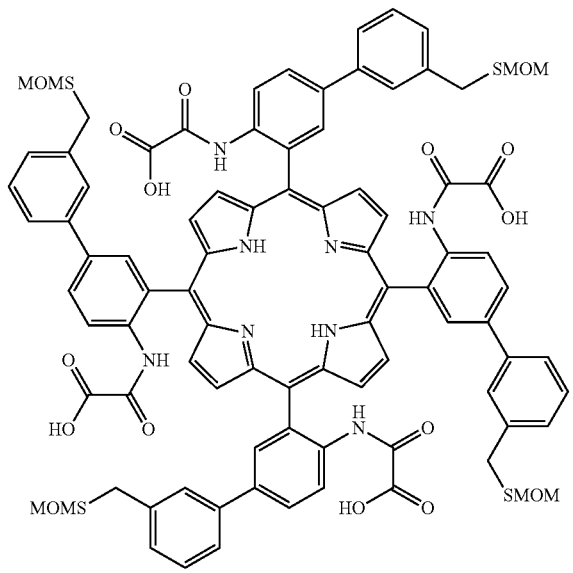

16

Example 17

The compound represented by the above formula 16 was dissolved in a mixed solvent of dichloromethane and ethanol (2:1), and 10 equivalents of $AgNO_3$ was added. After stirring overnight, the precipitated yellow powder was filtered and washed 3 times with 100 mL of dichloromethane. The powder was then added to 6 N HCl (20 mL), and chloroform (20 mL) was added. After stirring for 4 hours, the chloroform solution was collected and washed with water. Then, the solvent was removed by an evaporator, and the residue was purified by silica gel column chromatography to obtain a compound of the following formula 17. (Yield: 17%, MS (MALDI): m/z: 1507 [M]+)

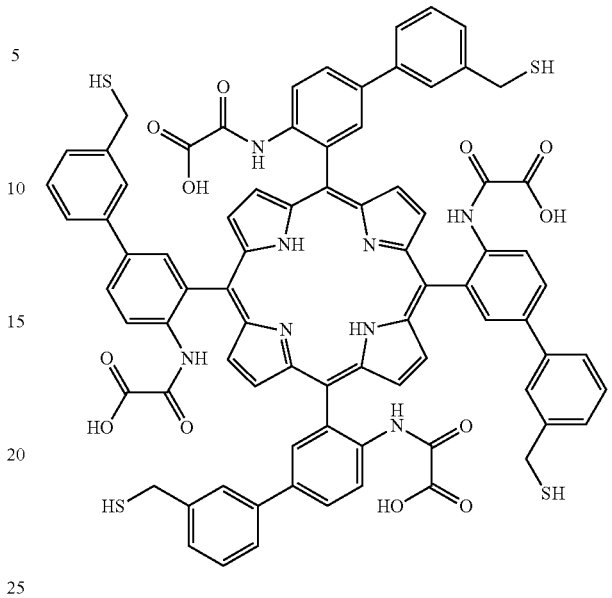

17

Photoelectric Conversion Efficiency Evaluation Test

An electrode film having a thickness of 100 nm and composed of $TiO_2$ nanoparticles was formed on an FTO substrate (length: 2 cm, width: 1 cm, FTO film thickness: 600 nm) produced by AGC Fabritech Co., Ltd. Further, the tetraphenylporphyrin derivative solution of Example 17 having a concentration of 600 μM was drop-cast thereon and then dried to form a $TiO_2$ thin film adsorbed with porphyrin. Further, a gold nanoparticle aqueous solution having a concentration of 1 nM was drop-cast thereon and then dried to obtain a solar cell.

An electrode was set in the alignment shown in FIG. 1, a xenon lamp was used as a light source (model number: R-300-3J, produced by Eagle Engineering Inc.), and a long-pass filter was placed 1 cm from the light source to face the light source. The solar cell obtained above was installed at a position further 11 cm away from the light source to face the light source, and then the current value under light irradiation was measured.

Figure 2:
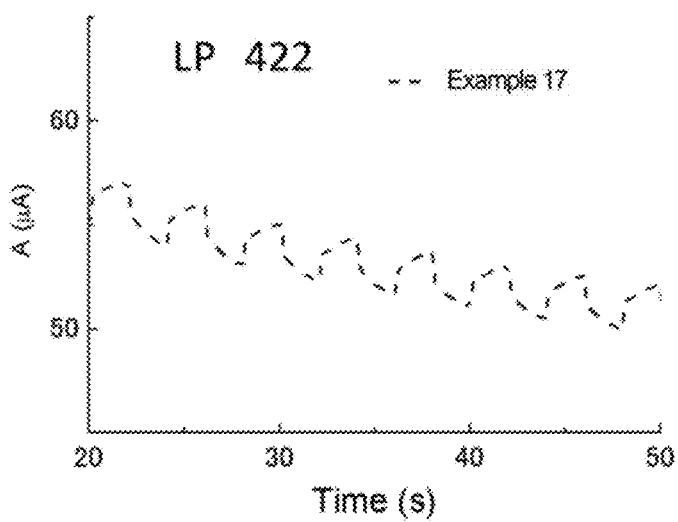
FIG. 2 shows the results of the photoelectric conversion evaluation test.

As shown in FIG. 2, the solar cell produced using the tetraphenylporphyrin derivative of Example 17 had excellent photoelectric conversion ability. From the above, it was suggested that the electrode film composed of $TiO_2$ nanoparticles and the layer comprising gold nanoparticle were bonded together more stably.

Example 18

The compound represented by the above formula 14 was dissolved in a mixed solvent of dichloromethane and ethanol (2:1), and 10 equivalents of $AgNO_3$ was added. After stirring overnight, the precipitated yellow powder was filtered and washed 3 times with 100 mL of dichloromethane. The powder was then added to 6 N HCl (20 mL), and chloroform (20 mL) was added. After stirring for 4 hours, the chloroform solution was collected and washed with water. Then, the solvent was removed by an evaporator, and the residue was purified by silica gel column chromatography to obtain a compound represented by the following formula 18. (Yield: 17%, MS (MALDI): m/z: 1164 [M]+)

18

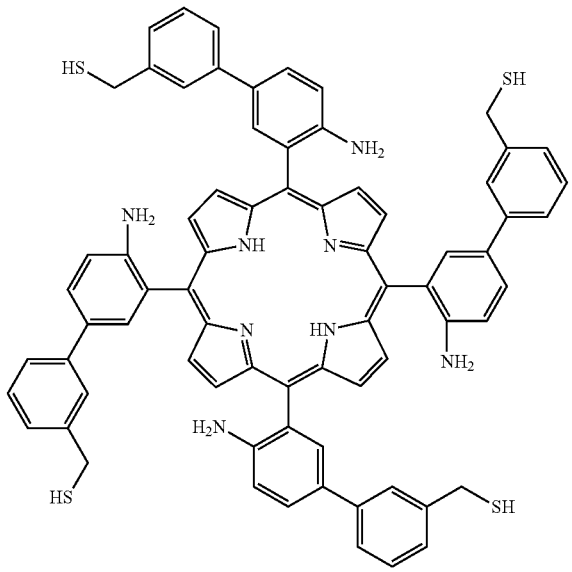

A commercially available polyimide film was washed with a cleaner (ES100, produced by JCU Corporation). The washed polyimide film was treated with ES200 (produced by JCU Corporation) to expose carboxyl groups on the surface. Thereafter, the obtained polyimide film was further treated with oxalyl chloride to obtain an acid chloride.

Production Example 1

Figure 3:
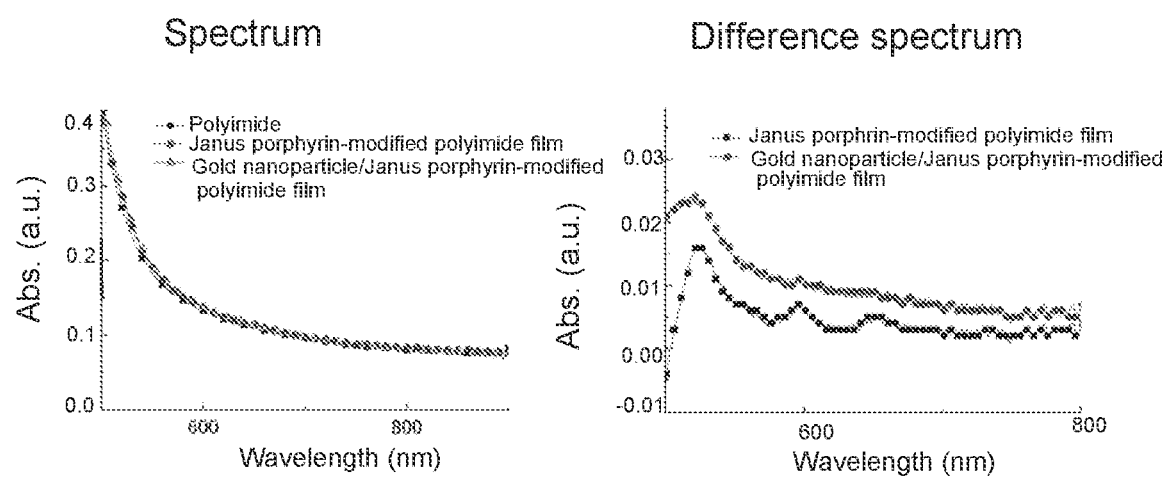
FIG. 3 shows the measurement results of absorption spectra.

The acid chloride of the polyimide film was immersed in a methylene chloride solution containing 10 mg of the tetraphenylporphyrin derivative of Example 18 and 100 μL of triethylamine. After stirring overnight, a tetraphenylporphyrin-modified polyimide film was obtained. When the absorption spectrum was measured using an absorptiometer, a spectrum of the tetraphenylporphyrin derivative was observed, as shown in FIG. 3. The term "Difference spectrum" in FIG. 3 means a difference spectrum between the absorption spectrum of the tetraphenylporphyrin-modified polyimide film and the absorption spectrum of the polyimide film.

Production Example 2

The tetraphenylporphyrin-modified polyimide film of Production Example 1 was immersed in a gold nanoparticle aqueous solution (1 μM) and stirred overnight, thereby obtaining a gold nanoparticle/tetraphenylporphyrin-modified polyimide film. When a difference spectrum between the absorption spectrum of the gold nanoparticle/tetraphenylporphyrin-modified polyimide film and the absorption spectrum of the polyimide film was measured in the same manner as in Production Example 1, an absorption spectrum of the gold nanoparticle/tetraphenylporphyrin derivative was observed, as shown in FIG. 3. The term "Difference spectrum" in Production Example 2 means a difference spectrum between the absorption spectrum of the gold nanoparticle/tetraphenylporphyrin-modified polyimide film and the absorption spectrum of the polyimide film.

Example 19

5-(Allyloxy)-2-nitrobenzaldehyde) was dissolved in acetic acid, and the solution was refluxed. Pyrrole was slowly added dropwise to the boiling solution, and boiling was then continued for 30 minutes. At the expiration of 30 minutes from the start of boiling, chloroform was added to the solution in order to avoid the formation of by-products. After the solution was naturally returned to room temperature, the glass container containing the solution was cooled by immersion in a container containing ice water. After standing overnight, the precipitated solid was collected and purified by silica gel chromatography (developing solvent: chloroform) to obtain a compound represented by the following formula 19.

(Yield: 10%, MS (MALDI): m/z: 1019 [M]+)

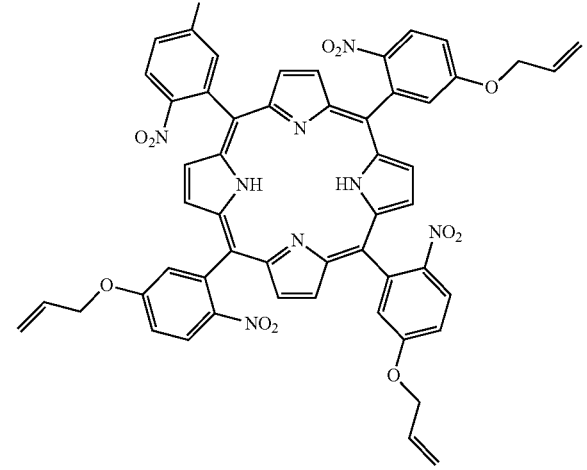

Example 20

After 1 g of the compound represented by the above formula 19 was dissolved in 100 mL of dichloromethane solution, 10 g of $SnCl_2$ was further added, and the resulting mixture was directly refluxed for 2 hours. 20 mL of 28 mass % aqueous ammonia solution was added to the resulting solution. After stirring, the aqueous phase was discarded, and the dichloromethane phase was removed by an evaporator to obtain a compound represented by the following formula 20.

(Yield: 10%, MS (MALDI): m/z: 899 [M]+)

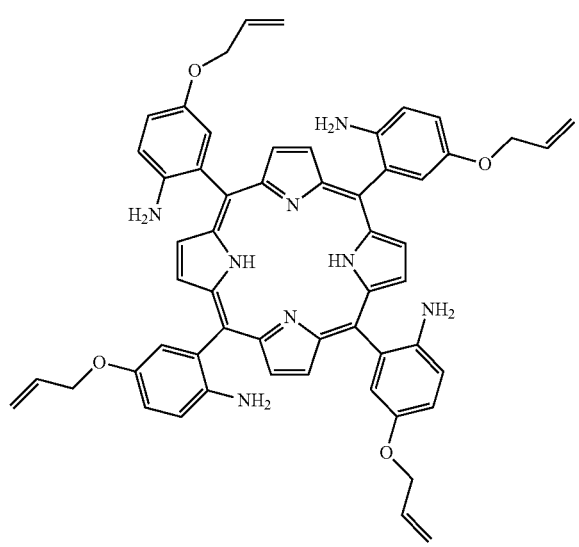

Example 21

1 g of the compound represented by the above formula 20 was dissolved in 100 mL of THF solution, and Ar was introduced. Further, an excess amount of triethoxysilane was added, and the temperature was raised to 80° C. Chloroplatinic acid was added, followed by stirring at 80° C. overnight. The obtained solution was purified to obtain a compound represented by the above formula 21.
(Yield: 10%, MS (MALDI): m/z: 2119 [M]+)

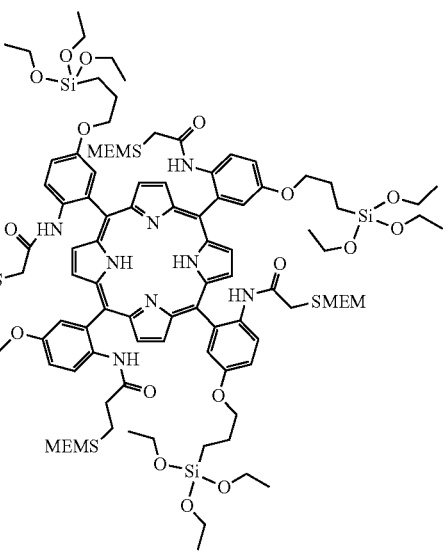

Example 22

Pyrrole and trifluoroacetic acid were added to S-(3-formyl-4-nitrophenyl)ethanethioate, followed by stirring for 1 hour. Then, chloranil was added, followed by stirring at 50° C. for 4 hours. After purification by column chromatography, 1 g of the obtained compound was dissolved in 100 mL of dichloromethane solution. Further, 10 g of SnCl$_2$ was added, and the resulting mixture was directly refluxed for 2 hours. 20 mL of 28 mass % aqueous ammonia solution was added to the resulting solution. After stirring, the aqueous phase was discarded, and the dichloromethane phase was removed by an evaporator, followed by purification by column chromatography, thereby obtaining a compound represented by the following formula 22. (Yield: 1%, MS (MALDI): m/z: 971 [M])+)

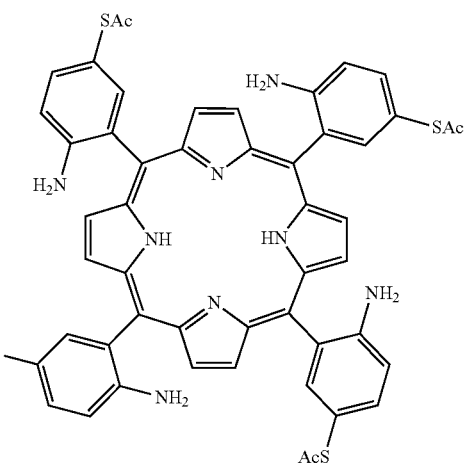

Example 23

After the compound represented by the above formula 22 was dissolved in a dichloromethane solution, an excess amount of methylamine was added, followed by stirring for 1 hour. The obtained solution was evaporated to obtain a compound represented by the following formula 23. (Yield: 100%, MS (MALDI): m/z: 803 [M]+)

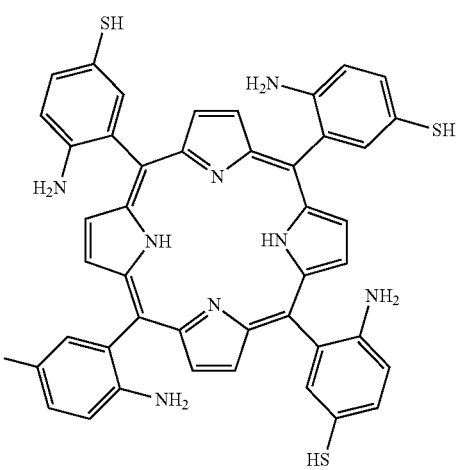

Example 24

The compound represented by the above formula 22 was dissolved in a THF solution and then ice-cooled. 4 equivalents of carbon disulfide and triethylamine were added, followed by stirring for 12 hours. The obtained solution was evaporated to obtain a compound represented by the following formula 24. (Yield 90%, MS (MALDI): m/z: 1274 [M]+)

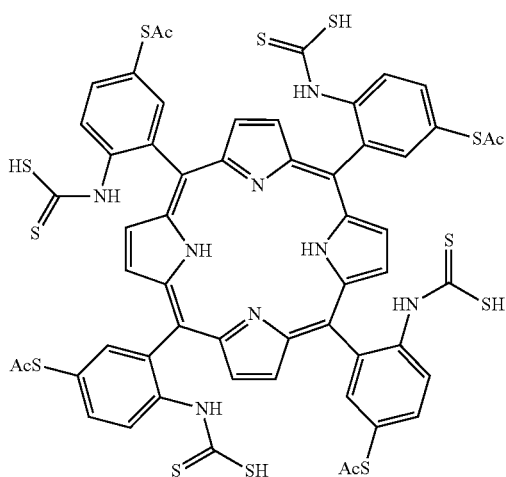

24

Example 25

The compound represented by the above formula 24 was dissolved in a THF solution and then ice-cooled. 4 equivalents of iodobenzene diacetate was added, followed by stirring for 1 hour. The solution was removed by evaporation, followed by purification by silica gel column chromatography, thereby obtaining a compound represented by the following formula 25. (Yield: 90%, MS (MALDI): m/z: 1139 [M]+)

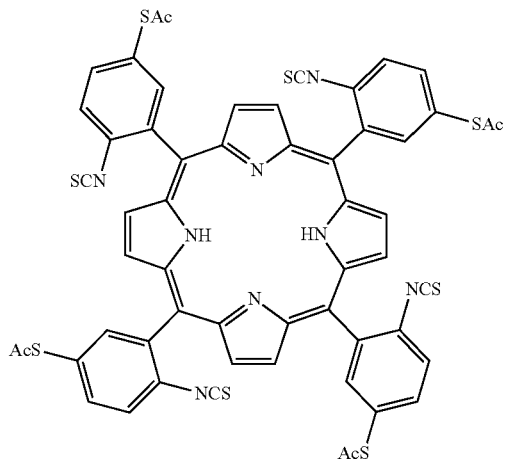

25

The invention claimed is:

1. A tetraphenylporphyrin derivative represented by the following formula (I):

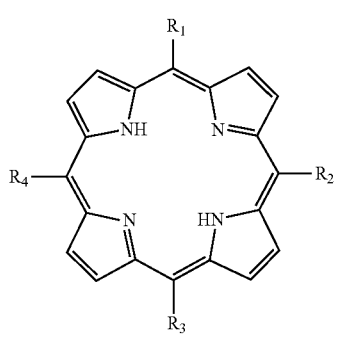

(I)

wherein in formula (I), $R_1$, $R_2$, $R_3$, and $R_4$ are each independently one substituent selected from the group consisting of the following formulas (II) to (IV) and (VI); and X and Y are any substituents that are different from each other:

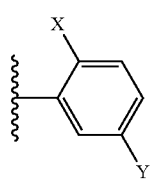

(II)

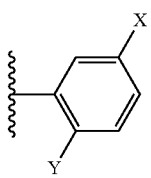

(III)

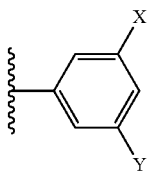

(IV)

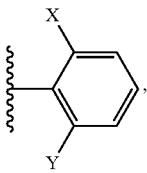

(VI)

in formulas (II) to (IV) and (VI), X and Y are each independently one member selected from the group consisting of an amino group, a catechol group, and a nitro group, and the following formulas (A) to (V):

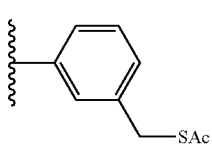

(A)

-continued

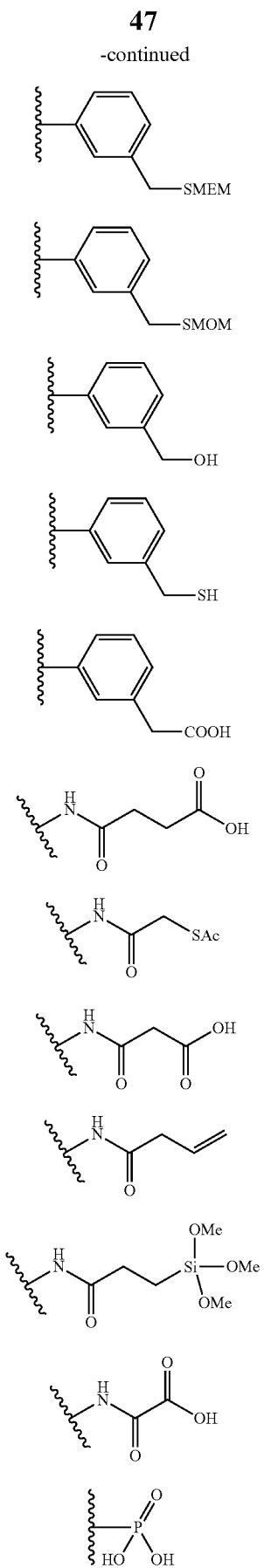

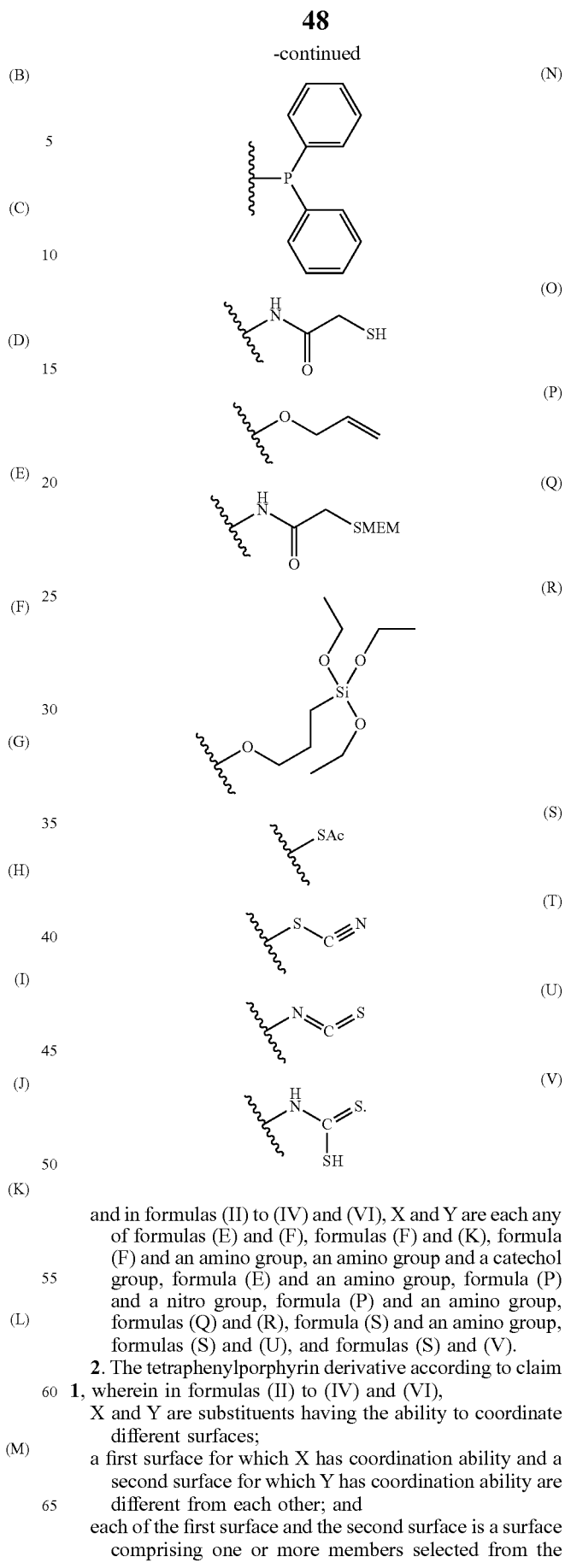

and in formulas (II) to (IV) and (VI), X and Y are each any of formulas (E) and (F), formulas (F) and (K), formula (F) and an amino group, an amino group and a catechol group, formula (E) and an amino group, formula (P) and a nitro group, formula (P) and an amino group, formulas (Q) and (R), formula (S) and an amino group, formulas (S) and (U), and formulas (S) and (V).

2. The tetraphenylporphyrin derivative according to claim 1, wherein in formulas (II) to (IV) and (VI),
X and Y are substituents having the ability to coordinate different surfaces;
a first surface for which X has coordination ability and a second surface for which Y has coordination ability are different from each other; and
each of the first surface and the second surface is a surface comprising one or more members selected from the group consisting of metal nanoparticles, semiconductor nanoparticles, and organic matter nanoparticles, or a bulk interface comprising one or more members selected from the group consisting of metals, semiconductors, and organic matter.

3. The tetraphenylporphyrin derivative according to claim 1, wherein in formula (I), $R_1$, $R_2$, $R_3$, and $R_4$ are all the same, and are each any one of formulas (II) to (IV) and (VI).

4. A complex comprising the tetraphenylporphyrin derivative according to claim 1 and one or more nanoparticles selected from the group consisting of metals, semiconductors, and organic matter.

5. A photoelectric conversion element having the complex according to claim 4.

* * * * *